United States Patent
Smyczynski

(10) Patent No.: US 8,858,880 B2
(45) Date of Patent: Oct. 14, 2014

(54) EXTRACORPOREAL PHOTODYNAMIC BLOOD ILLUMINATION (IRRADIATION) FOR THE TREATMENT OF CARBON MONOXIDE POISONING

(76) Inventor: Mark S. Smyczynski, Jefferson, MA (US)

( * ) Notice: Subject to any disclaimer, the term of this patent is extended or adjusted under 35 U.S.C. 154(b) by 0 days.

(21) Appl. No.: 13/372,380

(22) Filed: Feb. 13, 2012

(65) Prior Publication Data

US 2013/0101464 A1   Apr. 25, 2013

Related U.S. Application Data

(60) Provisional application No. 61/442,211, filed on Feb. 12, 2011.

(51) Int. Cl.
*A61M 1/32* (2006.01)
*A61M 1/36* (2006.01)

(52) U.S. Cl.
CPC ............... *A61M 1/3681* (2013.01); *A61M 1/32* (2013.01); *A61M 2202/0233* (2013.01)
USPC .......... 422/45; 604/5.02; 604/5.04; 604/6.09; 210/645

(58) Field of Classification Search
CPC ............................... A61M 1/32; A61M 1/3681
USPC ................. 604/5.04, 6.09, 6.11, 5.02; 422/45
See application file for complete search history.

(56) References Cited

U.S. PATENT DOCUMENTS 7,601,201 B2 * 10/2009 Fukutomi et al. .................. 95/46
2008/0147012 A1 * 6/2008 Rome ....................... 604/167.04

OTHER PUBLICATIONS

Weber, Martin. Handbook of Laser Wavelengths. New York: CRC Press, Jul. 1998.*

(Continued)

*Primary Examiner* — Leslie Deak
*Assistant Examiner* — Sara Sass
(74) *Attorney, Agent, or Firm* — Gerry A. Blodgett; David J. Blodgett; Blodgett & Blodgett, P.C.

(57) ABSTRACT

Treatment of carbon monoxide poisoning of a body by removal of a portion of the blood from the body, placing the portion in an exposure cell, exposing the portion in the cell to light of wave length and intensity that causes dissociation of carbon monoxide from hemoglobin, and returning the portion to the body. The intensity and wave length of the light is sufficient to dissociate a therapeutically-effective amount of carbon monoxide from the hemoglobin in the blood. The blood is circulated from and to the body through a concentric double lumen cannula. The wave lengths of the light are 540 and/or 570 nanometers. The cell exposes the blood to at least 9.5 Joules of dissociative light per milliliter of blood, and least 9.5 Watts of dissociative light per milliliter of blood per second. Oxygen is provided to, and the dissociated carbon monoxide is removed from the system.

18 Claims, 12 Drawing Sheets

(56) References Cited

OTHER PUBLICATIONS

Asimov, M.M., Asimov, R.M., and Rubinov, A.N, Spectrum of the Effect of Laser Radiation on Hemoglobin of the Blood Vessels of Skin, Journal of Applied Spectroscopy, vol. 65, No. 6, pp. 919-922, 1998.

Asimov, M.M., Asimov, R.M., and Rubinov, A.N, Laser-Induced Photodissociation of Carboxyhemoglobin for the Purpose of Treatment of an Organism Poisoned with Carbon Monoxide, Journal of Applied Spectroscopy, vol. 72, No. 3, pp. 454-457, 2005.

Asimov, M.M., Asimov, R.M., and Rubinov, A.N, Laser-Induced Photodissociation of Carboxyhemoglobin: An Optical Method for Eliminating the Toxic Effect of Carbon Monoxide, Optics and Spectroscopy, vol. 109, No. 2, pp. 237-275, 2010.

T. Riesbeck, H.J. Eichler, A High Power Laser System at 540 nm with Beam Coupling by Second Harmonic Generation, Optics Communications 275 (2007) 429-432.

Arens, Jutta. "HEXMO." Applied Medical Engineering. Web. Oct. 4, 2009. <http://www.ame.hia.rwth-aachen.de/index.php?id=267&L=1>.

* cited by examiner

Wattage Calculation Required for

Extracorporeal

Sustained

Photolysis

Mark S Smyczynski, MD

FIG 2

TRUE EQN $$\frac{I}{I_0} = e^{-\rho\sigma d} + \frac{q_\alpha}{q}\left[e^{-\rho\sigma d + qd} - e^{-\rho\sigma d}\right]$$

$$\sigma = \sigma_a + \sigma_s$$

FOR NON ABSORBING SCATTERERS $q = \rho\sigma_s$ $$\frac{I}{I_0} = e^{-\rho\sigma_a d}\left[e^{-\rho\sigma_s d} + \frac{q_\alpha}{q}\left(1 - e^{-\rho\sigma_s d}\right)\right]$$

FIG 3

$$\frac{I}{I_0} = e^{-\rho \sigma_a d} \left[ e^{-\rho \sigma_s d} + \frac{q_*}{q} \left(1 - e^{-\rho \sigma_s d}\right) \right]$$

$$\ln \frac{I}{I_0} = \ln \left\{ e^{-\rho \sigma_a d} \left[ e^{-\rho \sigma_s d} + \frac{q_*}{q} \left(1 - e^{-\rho \sigma_s d}\right) \right] \right\}$$

$$\ln \frac{I}{I_0} = \ln e^{-\rho \sigma_a d} + \ln \left[ e^{-\rho \sigma_s d} + \frac{q_*}{q} \left(1 - e^{-\rho \sigma_s d}\right) \right]$$

$$\ln \frac{I}{I_0} = -\rho \sigma_a d + \ln \left[ e^{-\rho \sigma_s d} + \frac{q_*}{q} \left(1 - e^{-\rho \sigma_s d}\right) \right]$$

$$-\ln \frac{I}{I_0} = \rho \sigma_a d - \ln \left[ e^{-\rho \sigma_s d} + \frac{q_*}{q} \left(1 - e^{-\rho \sigma_s d}\right) \right]$$

$$\ln \left(\frac{I}{I_0}\right)^{-1} = \rho \sigma_a d - \ln \left[ e^{-\rho \sigma_s d} + \frac{q_*}{q} \left(1 - e^{-\rho \sigma_s d}\right) \right]$$

$$\ln \frac{I_0}{I} = \rho \sigma_a d - \ln \left[ e^{-\rho \sigma_s d} + \frac{q_*}{q} \left(1 - e^{-\rho \sigma_s d}\right) \right]$$

FIG 4

$$\frac{I}{I_0} = e^{-\rho \sigma_a d} \left[ e^{-\rho \sigma_s d} + \frac{q_\alpha}{q} \left( 1 - e^{-\rho \sigma_s d} \right) \right]$$

$$\log \frac{I}{I_0} = \log \left\{ e^{-\rho \sigma_a d} \left[ e^{-\rho \sigma_s d} + \frac{q_\alpha}{q} \left( 1 - e^{-\rho \sigma_s d} \right) \right] \right\}$$

$$\log \frac{I}{I_0} = \log e^{-\rho \sigma_a d} + \log \left[ e^{-\rho \sigma_s d} + \frac{q_\alpha}{q} \left( 1 - e^{-\rho \sigma_s d} \right) \right]$$

$$\log \frac{I}{I_0} = (.434)(-\rho \sigma_a d) + \log \left[ e^{-\rho \sigma_s d} + \frac{q_\alpha}{q} \left( 1 - e^{-\rho \sigma_s d} \right) \right]$$

$$\log \frac{I}{I_0} = -(.434)(\rho \sigma_a d) + \log \left[ e^{-\rho \sigma_s d} + \frac{q_\alpha}{q} \left( 1 - e^{-\rho \sigma_s d} \right) \right]$$

$$-\log \frac{I}{I_0} = (.434)(\rho \sigma_a d) - \log \left[ e^{-\rho \sigma_s d} + \frac{q_\alpha}{q} \left( 1 - e^{-\rho \sigma_s d} \right) \right]$$

$$\log \left( \frac{I}{I_0} \right)^{-1} = (.434)(\rho \sigma_a d) - \log \left[ e^{-\rho \sigma_s d} + \frac{q_\alpha}{q} \left( 1 - e^{-\rho \sigma_s d} \right) \right]$$

$$\log \frac{I_0}{I} = (.434)(\rho \sigma_a d) - \log \left[ e^{-\rho \sigma_s d} + \frac{q_\alpha}{q} \left( 1 - e^{-\rho \sigma_s d} \right) \right]$$

$$OD = (.434)(\rho \sigma_a d) - \log \left[ e^{-\rho \sigma_s d} + \frac{q_\alpha}{q} \left( 1 - e^{-\rho \sigma_s d} \right) \right]$$

FIG 5

AT 540 nm INCIDENT PHOTONS $\sigma_a$ & $\sigma_s$ ARE RELATED SUCH THAT $\sigma_a$ IS A MAXIMUM & $\sigma_s$ A MINIMUM AND $$\ln \frac{I}{I_0} = \ln e^{-\rho \sigma_a d} + \ln \left[ e^{-\rho \sigma_s d} + \frac{q_L}{q} \left(1 - e^{-\rho \sigma_s d}\right) \right]$$

CAN BE APPROXIMATED IN THE 540 nm REGION BY $$\ln \frac{I}{I_0} = \ln e^{-\rho \sigma_a d}$$

$$\ln \frac{I}{I_0} = -\rho \sigma_a d$$

$$e^{\ln \frac{I}{I_0}} = e^{-\rho \sigma_a d}$$

$$\frac{I}{I_0} = e^{-\rho \sigma_a d}$$

FIG 6

FOR HUMAN BLOOD $\rho \leftrightarrow [H_gB]$ IN $mM/L$ = $9\ mM/L$ $\sigma_a \leftrightarrow \epsilon_{H_gB}$ IN $L/mM\,cm$ = $15.5\ L/mM\,cm$  AT  $540\ nm$ $d \leftrightarrow x$ IN $cm$ = $x\ cm$ $$\frac{I}{I_0} = e^{-\rho \sigma_a d} \quad \leftrightarrow \quad \frac{I}{I_0} = e^{-[H_gB]\,\epsilon_{H_gB}\,x}$$

$$[H_gB]\,\epsilon_{H_gB} = (9\ mM/L)(15.5\ L/mM\,cm) = 139.5/cm$$

$$\frac{I}{I_0} = e^{-(139.5/cm)(.01\ cm)}$$

$$\frac{I}{I_0} = e^{-1.395} = .2478 \approx .25$$

AT $x = .013\ cm$ $$\frac{I}{I_0} = e^{-(139.5/cm)(.013\ cm)} = e^{-1.8135} = .16$$

WHAT IS THE VOLUME OF A THIN DISK OF FLUID 10 cm IN DIAM & 0.01 cm THICK $$A = \pi (5 cm^2) = 78.54 \ cm^2$$

$$V = (78.54 \ cm^2)(.01 cm) = .7854 \ cm^3$$

AND FOR $D_{IAM}$ OF 10 cm & THICKNESS 0.013 cm $$V = (78.54 \ cm^2)(.013 cm) = 1.02 \ cm^3 \approx 1 \ cm^3$$

ASSUME 1 $cm^3$ WHOLE BLOOD = 1 mL

No. OF HgB MOLECULES IN 1 mL OF BLOOD $$\left(9 \frac{mM}{L}\right)\left(\frac{1 L}{10^3 mL}\right)\left(\frac{1 mL}{1}\right)\left(\frac{1 M}{10^3 mM}\right)\left(\frac{6.023 \times 10^{23}}{M}\right)$$

$$= \frac{(9)(6.023)}{1} \times 10^{23} \times 10^{-6}$$

$$= 54.21 \times 10^{17} = 5.421 \times 10^{18} \ \text{No of HgB}/1 mL$$

FIG 8

$$E = h\nu = \frac{hc}{\lambda}$$

$$= \frac{(6.6262 \times 10^{-34} \text{ J·sec})(3 \times 10^8 \text{ M/sec})}{540 \times 10^{-9} \text{ M}}$$

$$= \frac{(6.6262)(3)}{540} 10^{-34+8+9}$$

$$= .0368 \times 10^{-17} \text{ J}$$

$$= .368 \times 10^{-18} \text{ J/PHOTON} \quad (E \text{ of } 1 \text{ PHOTON})$$

$$1 \text{ J/sec} = 1 \text{ WATT}$$

$$(1 \text{ J/sec})\left(\frac{\text{PHOTON}}{.368 \times 10^{-18} \text{ J}}\right) = 2.72 \times 10^{18} \text{ PHOTONS/sec}$$

FIG 9

For photons of wavelength $540 \times 10^{-9}$ m, each watt contains $2.72 \times 10^{18}$ photons/sec.

In whole blood, concentration of $HgB$ is $5.421 \times 10^{18}$ HgB's/mL

---

The volume under consideration for this calculation is a thin disk 10 cm in diameter and .013 cm thick, equal to $\approx 1$ cm$^3$.

At a depth of .013 cm for incident photons of wavelength $540 \times 10^{-9}$ m, 84% of the photons are absorbed.

---

We now make one assumption that there is a one to one quantum relationship between a photon absorbed and photolysis.

FIG 10

We are interested in a RATE REACTION, i.e. Watts must relate to flow.

OR  $J/sec \longleftrightarrow mL/sec$

FIG 11

Consider a flow of $1\ mL/sec$ $$(5.421 \times 10^{18}\ HgB's/mL)(1\ mL/sec) = 5.421 \times 10^{18}\ HgB's/sec$$

And we wish to know how many watts are needed to react this many HgB's.

For $540 \times 10^{-9} m$ wavelength photons we write $$(N\ J/sec)\left(\frac{photon}{.368 \times 10^{-18}\ J}\right)(.84) = 5.421 \times 10^{18}\ HgB's/sec$$

$$(N\ J/sec)\left(2.72 \times 10^{18}\ \frac{photon}{J}\right)(.84) = 5.421 \times 10^{18}\ HgB's/sec$$

(percent absorbed)

$$(N\ J/sec)\left(2.72 \times 10^{18}\ \frac{photon}{J}\right) = 6.454 \times 10^{18}\ HgB's/sec$$

$$N \frac{J}{sec} = \frac{6.454 \times 10^{18} \; HgB/sec}{2.72 \times 10^{18} \; photon/J}$$

$$N \frac{J}{sec} = 2.37 \left(\frac{HgB}{photon}\right)\left(\frac{J}{sec}\right)$$

∴ Number of Watts for 1 HgB/photon = $\boxed{2.37}$

---

ADDENDUM

However there are 4 binding sites/HgB and we have assumed 1 photon/binding site

Thus (from above)

$$N \frac{J}{sec} = 2.37 \left(\frac{HgB}{photon}\right)\left(4 \frac{binding\;site}{HgB}\right)\left(1 \frac{photon}{binding\;site}\right)\left(\frac{J}{sec}\right)$$

$$\underline{\underline{N = 9.48}}$$

FIG 12

EXTRACORPOREAL PHOTODYNAMIC BLOOD ILLUMINATION (IRRADIATION) FOR THE TREATMENT OF CARBON MONOXIDE POISONING

CROSS-REFERENCE TO RELATED APPLICATIONS

This application claims the benefit under 35 U.S.C. §119(e) of U.S. Provisional Application No. 61/442,211 filed Feb. 12, 2011, which is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

This invention involves a system for treating carbon monoxide poisoning.

BACKGROUND OF THE INVENTION

Carbon monoxide (CO) poisoning is a well-known phenomenon, and for the most part, its pathophysiology is well-understood. Each year in the United States there are close to 500 deaths, over 15,000 emergency room visits, and approximately 4,000 hospitalizations due to CO poisoning. A review of pertinent background information on the subject can be found at the following Internet links. http://www.cdc.gov/co/faqs.htm, and http://en.wikipedia.org/wiki/Carbon_monoxide_poisoning Current Treatment: At present, the treatment of CO poisoning can be thought of as having three main components: first aid, standard oxygen therapy, and hyperbaric oxygen. First aid consists of immediately removing the victim from the source of CO exposure. Standard oxygen therapy consists of administering 100% oxygen through a tight-fitting non-rebreather mask. This technique results in the administration of high concentrations of oxygen at a level of between 60-90% $O_2$. However, for patients with severe chronic obstructive pulmonary disease (COPD) such high levels of oxygen can actually inhibit their respiratory drive and thus lead to decreased ventilation. Hyperbaric oxygen (HBO) requires the use of a hyperbaric chamber which is found in very select locations and is not always readily available. However, a review published in 2005 on the use of HBO concluded: "There is conflicting evidence regarding the efficacy of HBO treatment for patients with CO poisoning. Methodological shortcomings are evident in all published trials, with empiric evidence of bias in some, particularly those that suggest a benefit of HBO. Bayesian analysis further illustrates the uncertainty about a meaningful clinical benefit. Consequently, firm guidelines regarding the use of HBO for patients with CO poisoning cannot be established. Further research is needed to better define the role of HBO, if any, in the treatment of CO poisoning."

Scientific Background: Following exposure, CO binds to hemoglobin to form carboxyhemoglobin. The affinity between CO and hemoglobin is approximately 230 times stronger than the affinity between oxygen and hemoglobin. Therefore, CO binds to hemoglobin in a much greater likelihood than oxygen. Carbon monoxide also binds to the heme-protein known as myoglobin. Carbon monoxide also has a high affinity for myoglobin at about 60 times greater than that of oxygen. It should also be noted that a delayed return of symptoms of CO poisoning have been reported and is associated with a recurrence of increased carboxyhemoglobin levels following an initial reduction in the level of carboxyhemoglobin. This effect may be due to a late release of CO from myoglobin, which then subsequently binds to hemoglobin.

Although previously not associated with carbon monoxide poisoning, the basic principle of extracorporial therapy involves the circulation of blood outside of the body. Extracorporial treatment is well-established in the practice of medicine, and the most well-known example is hemodialysis. Another common example is cardiac bypass surgery during which an external pump is used instead of the heart which allows surgeons to operate on a non-beating heart. Two less well-known examples are plasmapharesis and peripheral blood stem-cell harvest.

The application that may appear most pertinent in the setting of CO poisoning is the extracorporeal membrane oxygenator (ECMO). These devices have been shown to play an important role in the clinical management of neonatal infants whose lungs are not developed enough to provide the physiologic function of oxygen absorption and carbon dioxide excretion. An example of such a device and a brief description of its principles of operation can be found at the following Internet link. http://www.ame.hia.rwth-aachen.de/index.php?id=267&type=98&L=1&L=1

It should be noted that the administration of 100% oxygen through a tight-fitting non-rebreather mask reduces the elimination half-life of carboxyhemoglobin to an average of 60 minutes, while HBO at a pressure of between 2.4 and 3 atmospheres reduces the elimination half-life of carboxyhemoglobin to an average of 20 minutes. Based on a five half-life carboxyhemoglobin elimination end-point, this would on average require five hours of 100% oxygen administration or 100 minutes of HBO at pressures noted above.

All of the existing treatments for carbon monoxide poisoning have some drawbacks. These and other difficulties experienced with the prior art devices have been obviated in a novel manner by the present invention.

It is, therefore, an outstanding object of some embodiments of the present invention to provide a system for the treatment of carbon monoxide poisoning in an efficient and effective manner.

Another object of some embodiments of the present invention is to provide a system for the treatment of carbon monoxide poisoning in a cost effective manner.

With these and other objects in view, as will be apparent to those skilled in the art, the invention resides in the combination of parts set forth in the specification and covered by the claims appended hereto, it being understood that changes in the precise embodiment of the invention herein disclosed may be made within the scope of what is claimed without departing from the spirit of the invention.

BRIEF SUMMARY OF THE INVENTION

An extracorporial treatment of carbon monoxide poisoning of a body by removal of a portion of the blood from the body, placing the portion in an exposure cell, exposing the portion in the cell to light of wave length and intensity that causes dissociation of carbon monoxide from hemoglobin, and returning the portion to the body. The intensity and wave length of the light is sufficient to dissociate a therapeutically-effective amount of carbon monoxide from the hemoglobin in the blood. The blood is circulated from and to the body through a concentric double lumen cannula. The wave lengths of the light are 540 and/or 570 nanometers. The cell exposes the blood to at least 9.5 Joules of dissociative light per milliliter of blood, and at least 9.5 Watts of dissociative light per milliliter of blood per second. Oxygen is provided to the system, and the dissociated carbon monoxide is removed from the system.

BRIEF DESCRIPTION OF THE DRAWINGS

The character of the invention, however, may best be understood by reference to one of its structural forms, as illustrated by the accompanying drawings, in which:

FIG. 2 through 12 shows the calculations used to determine the intensity of the desired dissociative light and of the desired wattage of the laser.

DETAILED DESCRIPTION OF THE INVENTION

Figure 1:
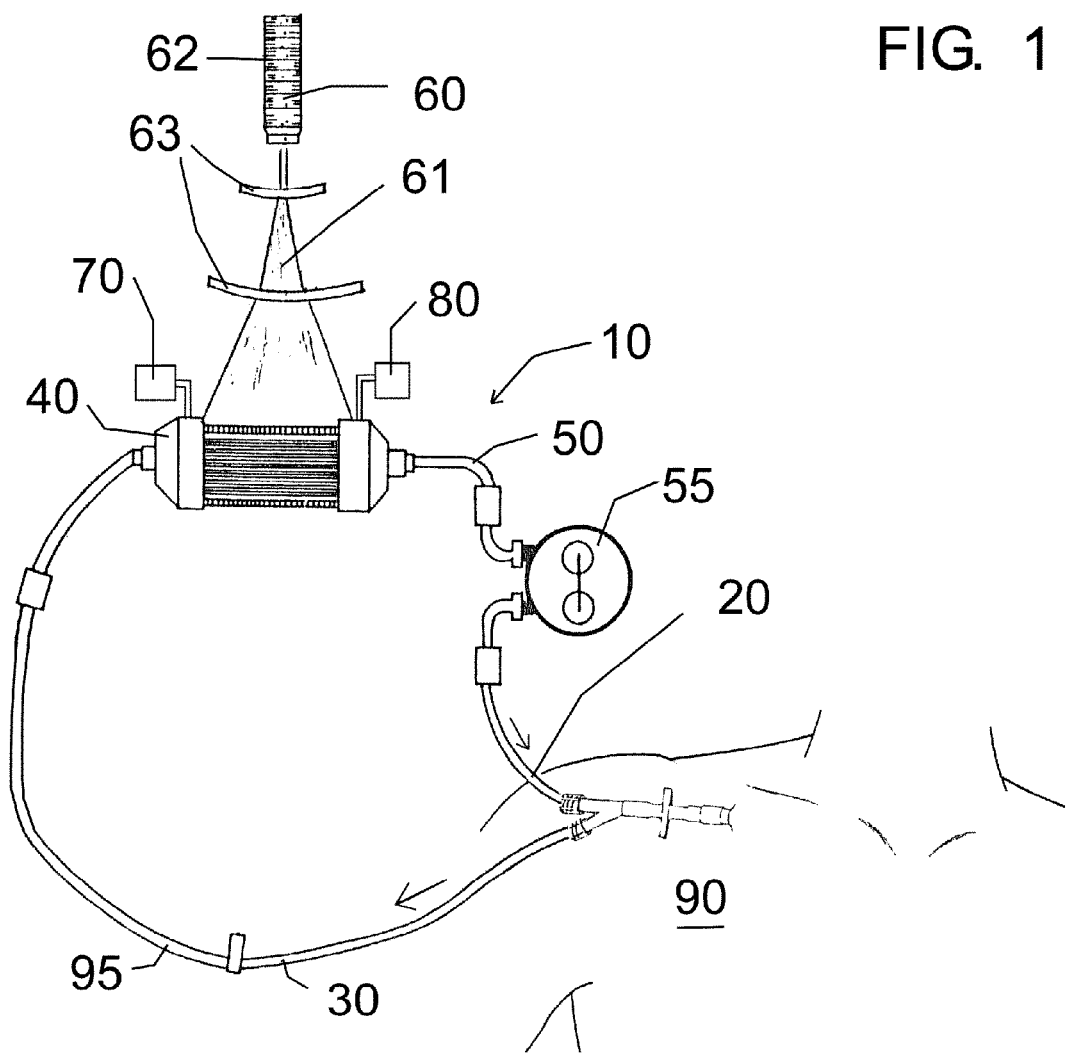
FIG. 1 shows a schematic diagram of a system for treating carbon monoxide poisoning and representing one embodiment of the present invention.

Referring first to FIG. 1 in which the general principles of the present invention are shown, the carbon monoxide treatment system is designated by the numeral 10. The human body is designated by numeral 90. The cannula 20 is inserted into the human 90. The cannula 20 includes a outgoing leg 30 that takes blood 95 out of the body 90, and an incoming leg 50 that puts blood 95 back into the body 90. A cell 40 is positioned between the outboard ends of the outgoing 30 and incoming leg 50 and the blood 95 is circulated through the cell 40. A blood pump 55 in the incoming leg 50 causes the circulation of the blood 95 through the cannula 20.

The cell 40 visually presents the circulating blood 95 to the beam 61 of a laser system 60, that includes the laser 62 itself, and a beam control system 63. An oxygen injector 70 feeds oxygen into the cell 40. A carbon monoxide extractor 80 removes carbon monoxide from the cell 40.

Photochemical research dating back to the 1970's has shown that visible light, particularly in the green portion of the spectrum at the wavelength of 540 nanometers, causes the photodissociation of CO from carboxyhemoglobin. It is upon this principle that this novel approach to the treatment of CO poisoning is based.

When the concept of this new approach in the treatment of CO poisoning was first envisioned, there was a significant technological barrier. An initial calculation was made regarding the amount of visible light that would be required at the 540 nanometer wavelength in order to provide an advantage over standard oxygen therapy and with the approximate equivalence of HBO in the treatment of CO poisoning. Expressed in terms of wattage, and assuming 100% efficiency at a blood flow rate of one milliliter per second, 9.5 Watts of visible light at 540 nanometers is necessary. However, xenon arc lamps and tunable dye lasers were between one and three orders of magnitude below this requirement. Recently, a high power laser system at 540 nanometers with beam coupling by second harmonic generation has been described capable of generating a single beam with an average power of 124 Watts. T. Riesbeck, H. J. Eichler, A High Power Laser System at 540 nm with Beam Coupling by Second Harmonic Generation, Optics Communications 275 (2007) 429-432.

Description and Principles of Apparatus: Based on that which is described above, it becomes a straightforward concept to apply the robust fluence of the visible light generated by the high power laser system at 540 nanometers to an apparatus that is analogous to an ECMO-like device while simultaneously providing standard oxygen therapy. For the discussion which follows, the yet-to-be-named apparatus shall simply be referred to as an "ECMO-like device". It is important to recognize that the antidote to CO poisoning is oxygen. For maximum effectiveness, oxygen would be introduced to the patient by both the tight-fitting non-rebreather mask and by the ECMO-like device in which the CO is photodissociated from the carboxyhemoglogin to subsequently form oxyhemoglobin. This underlying principle can essentially be understood as "photodialysis" and is supported by technology that currently exists and which can be applied, modified, and improved upon.

Optimal Design Issues: There are multiple aspects that must be considered in order to optimize the efficacy of the apparatus as a whole. These relate to the configuration and propagation of the beam produced by the laser, the blood-light contact surface area, the semipermeable membranes within the ECMO-like device, the rate of extraporporeal circulation, and the degree of invasiveness of the procedure itself.

Invasiveness: The invasiveness can easily be kept to a minimum by using a double-lumen central-line catheter. Central-lines are commonly placed in patients on a daily basis throughout the country. There are several approaches that include the jugular, subclavian, and femoral veins. Using the femoral vein is often considered as the safest and easiest. The blood is best removed from the proximal port of the double-lumen catheter and returned to the patient by way of the distal port of the catheter. This reduces the likelihood of mixing successfully treated blood with untreated blood.

Extracorporial Circulation Rate: A low priming volume is optimal in order to minimize the amount of blood that is outside of the body and not inside the ECMO-like device. However, the most important considerations relate to the volume of blood and its rate of flow inside the ECMO-like device. Determining the optimal volume and flow rate of blood inside the ECMO-like device will be a matter of precise engineering since it is within the ECMO-like device that the photodissociation occurs. There are other additional factors pertinent to this aspect which are described below. Additionally, one or more heat exchangers should be incorporated into extracorporeal circuit in order to maintain the warmth of the blood and prevent a lowering of core body temperature.

Semipermeable Membranes: Any semipermeable membrane that is used must be of a generally small diameter or thickness to facilitate the displacement and release of CO following its photodissociation from carboxyhemoglobin, its replacement with oxygen, and the subsequent removal of the CO. In addition, all semipermeable membranes in use must be completely transparent to visible light at the 540 nanometer wavelength.

Blood-Light Contact Surface Area: As noted above, the photochemical reaction resulting in the photodissociation of CO from carboxyhemoglobin is highly optimized at the 540 nanometer wavelength. With the understanding that attenuation of light occurs through the processes of absorption and scatter, it would be expected that the light from the laser would be significantly attenuated in a thin layer of blood and not penetrate that deeply before becoming almost completely absorbed. Thus the photochemical reaction resulting in the photodissociation of CO is essentially a "surface phenomena". This supports the fact that the blood-light contact surface area be made as large as possible in order to optimize the absorption of the laser light as it will mostly occur in a "thin sheet" of blood.

Propagation and Configuration of Laser Light: Based on the above, there are several approaches that can be taken to propagate and configure the light from the laser both in terms of the blood-light contact surface area and the semipermeable membranes through which the blood flows. One possible approach could involve designing the semipermeable membranes as a thin layer of two sheets between which the blood flows. In this situation, the light from the laser would need to be passed through one or more beam expanders to create a large two-dimensional cross-section that matches the surface area of the semipermeable membranes. As an additional improvement to using a single expanded beam, a beam splitter can be used to first generate two beams. Then with the use of mirrors and two sets of beam expanders, it should be possible to illuminate the semipermeable membranes from both sides. This capability would be expected to allow for a greater separation between the two semipermeable membrane sheets which in turn would impact the volume of blood in the ECMO-like device and its extracorporeal rate of flow. Another approach could involve propagating the light from the laser directly into the ECMO-like device using fiber-optic technology. Then by using a series of branching fiber-optic pipes of decreased diameter, the laser light could be made to illuminate an array of semipermeable membranes configured as small diameter tubes inside of which the blood flows. The fiber-optic pipes and semipermeable membrane tubes would be engineered in such a way so as to form a three-dimensional structure so that when illuminated, all of the light produced by the laser is utilized. With the use of fiber-optic technology as described, which is essentially an "inside-out" approach, the ECMO-like device would likely be more compact. Additionally, there may be greater flexibility in terms of the volume of blood inside the ECMO-like device and the corresponding extracorporeal flow rate. Using fiber-optics in some capacity would also reduce or eliminate the use of mirrors, beam splitters, and beam expanders.

Medical Benefits of Effective Treatment of CO Poisoning: Simply stated, the greatest benefit of successful treatment of CO poisoning is the prevention of patient death. As noted in the opening paragraph, there are approximately 500 deaths per year from CO poisoning in the United States. Unfortunately, in the majority of cases of severe CO poisoning, patient death neither can nor will be avoided. However, with the modest assumption that 20% of the deaths can be prevented with prompt and effective treatment using a readily available intervention such as the ECMO-like device as described, one hundred lives might be saved. This corresponds to saving two lives each week on average.

While a reduction in mortality is perhaps the most obvious and immediate benefit of prompt intervention using the ECMO-like device, an equally valuable benefit lies with the prevention of medical complications from severe CO poisoning in those who survive. It is well-described in the literature that CO poisoning often results in significant toxicity to the central nervous system (CNS). Most of the damage from CO poisoning in the CNS is believed to occur in the white matter. Moreover, the effects of significant CO poisoning in the CNS are often irreversible and result in neurologic disability. The long-lasting CNS complications from CO poisoning can leave individuals with permanent neurological deficits that require long-term rehabilitation. Given the fact that there are over 4000 hospitalization each year in the United States due to CO poisoning, the additional cost associated with the life-long care of those affected with neurologic disability from CO poisoning can easily reach into the tens of millions of dollars. Thus in addition to its life-saving benefit in the setting of severe CO poisoning, the ECMO-like device would be expected to make a profound impact in reducing, and in some cases eliminating CNS complications and thereby prevent serious long-term neurological deficits in survivors.

Although not as dramatic as the CNS complications, CO poisoning can also result in cardiac toxicity. Once again, and analogous to what is described in the above paragraph, the ECMO-like device would be expected to favorably reduce the likelihood of permanent heart damage.

Theoretical Considerations: In considering aspects by which the ECMO-like device might be optimally applied, a few circumstances warrant consideration. In the hospital setting, one might envision using several ECMO-like devices while simultaneously administering HBO. In this situation, the patient would be required to be inside a hyperbaric chamber with two or more double-lumen catheters placed as central-lines in either the jugular, subclavian, or femoral veins and with each one connected to an ECMO-like device. While this seemingly represents "maximum effective therapy", the practicality of this approach is rather questionable and its true advantage is likely in doubt. In the prehospital setting, one might envision a more useful application. Emergency medical service (EMS) personnel are currently trained in various life-saving techniques which include cardiac defibrillation and starting peripheral intravenous lines. With technological advances, the ECMO-like device will likely become more miniaturized, both in terms of the laser light source and all of the associated engineering. Once the diagnosis of CO poisoning is made, paramedicics would be able to initiate the photodissociation by using a suitable double-lumen catheter along with standard oxygen therapy. Actions taken in this regard by EMS personnel well in advance of their arrival to the hospital are not only logistically possible, but would also provide a genuine time advantage in terms of maximizing the available and effective treatment of CO poisoning in the prehospital setting.

In the preferred embodiment of the invention, the cell would be provided with a system to inject oxygen into the cell and treated blood. This would encourage the hemoglobin, from which the carbon monoxide has been dissociated, to take up oxygen. That would discourage reassociation of dissociated carbon monoxide back into the hemoglobin.

Also, in the preferred embodiment of this invention, the cell in which the carbon monoxide would be dissociated from the blood is provided with a venting system that would capture and isolate the dissociated carbon monoxide from the cell. This would reduce the back-pressure of the carbon monoxide in the cell from slowing the dissociation. Furthermore, preferred system would prevent the venting of the carbon monoxide into the environment of the equipment. This same principle should be applied to other, existing carbon monoxide treatment systems. The conventional high pressure oxygen mask, used in an emergency room, vents the dissociated carbon monoxide into the room. This exposes the other emergency room people, including the patients and staff, to the carbon monoxide. The cumulative and long-term aspects of carbon monoxide poisoning, and the special vulnerability of certain types of patients, suggest that this unmanaged venting to the carbon monoxide to the emergency room may not be desirable.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desire to secure by Letters Patent is:

1. A system for treatment of carbon monoxide poisoning of the blood of a living victim, comprising:
   a. an exposure cell,
   b. a first sub-system engineered adapted to remove a portion of the whole blood from the victim, said whole blood containing hemoglobin to which carbon monoxide is associated, and to place the portion of whole blood in the exposure cell,
   c. a second sub-system adapted to expose the portion in the cell to dissociative light that causes dissociation of carbon monoxide from hemoglobin, wherein the dissociative light is of a wavelength selected from the group of 540 and 570 nanometers and combinations thereof, and the dissociative light is of an intensity of at least 9.5 Joules per milliliter of blood, from which the carbon monoxide has been dissociated from the hemoglobin, and
   d. a third sub-system adapted to return the portion of whole blood to the victim, without the carbon monoxide.

2. A system as recited in claim 1, wherein the dissociative light is of an intensity of at least 9.5 Watts per milliliter of blood flow per second, through the exposure cell.

3. A system as recited in claim 1, wherein the first and third sub-systems are a concentric double lumen cannula, capable of removing blood from and return to the victim at 500 ml per minute.

4. A system as recited in claim 1, wherein the system includes a subsystem that injects gaseous oxygen into the cell, and a subsystem that maintains the temperature of the blood in the exposure cell below the temperature that the blood or system degrades.

5. A system as recited in claim 1, wherein the system includes a subsystem that captures and isolates the disassociated carbon monoxide, from the blood and the environment of the system.

6. A system as recited in claim 1, wherein the exposure cell includes two semipermeable membranes as a thin layer of two parallel sheets between which the blood flows, and through which the dissociative light passes.

7. A system as recited in claim 1, wherein the source of the dissociative light is a laser, that produces a beam of light that illuminates the exposure cell, and the system includes a beam expander between the laser and the exposure cell, to expand the cross-section of the beam, to expand the surface area of the exposure cell illuminated by the beam.

8. A system as recited in claim 1, wherein the source of the dissociative light is a laser, that produces a beam of light that illuminates the exposure cell, and the system includes a beam splitter, and mirrors, arranged to first split the beam into two beams, and then, using the mirrors, use one of the beams to illuminated the back side of the exposure cell.

9. A system as recited in claim 1, wherein the source of the dissociative light is a laser, that produces a beam of light that illuminates the exposure cell, and the system includes a beam splitter, and fiberoptic cable, arranged to first split the beam into two beams, and then, using the fiberoptic cable, use one of the beams to illuminated the back side of the exposure cell.

10. A system as recited in claim 1, wherein the source of the dissociative light is a laser, that produces a beam of light that illuminates the exposure cell, and the system includes a series of branching fiberoptic pipes of decreased diameter, through which the dissociative light flows, so that the dissociative light is made to illuminate an array of semipermeable membranes configured as small diameter tubes inside of which the blood flows.

11. A system as recited in claim 1, wherein the source of the dissociative light is a laser, that produces a beam of light that illuminates the exposure cell, and the exposure cell includes a plurality of fiberoptic pipes and a plurality of semipermeable membrane tubes containing blood, the pipes and tubes being engineered so as to form a three-dimensional structure of alternating pipes and tubes, so that, when the dissociative light passes through the fiberoptic pipes, the light illuminates the tubes that surround each pipe.

12. A method for treatment of carbon monoxide poisoning of a living victim of carbon monoxide poisoning, comprising the steps of:
   a. removing a portion of the whole blood from the circulatory system of a victim of carbon monoxide poisoning, said portion of whole blood containing carbon monoxide associated with the victim's hemoglobin in the portion of the whole blood,
   b. placing the portion of the whole blood in an exposure cell,
   c. exposing the portion of the whole blood in the exposure cell to dissociative light that causes dissociation of carbon monoxide from hemoglobin, wherein the source of the dissociative light is a laser, where the dissociative light is of a wavelength selected from the group of 540 and 570 nanometers and combinations thereof, and the dissociative light is of an intensity of at least 9.5 Joules per milliliter of blood,
   d. separating the dissociated carbon monoxide from the portion of the whole blood, and
   e. returning the portion of whole blood from which carbon monoxide has been separated, to the victim's circulatory system.

13. A method as recited in claim 12, wherein the dissociative light is of a intensity of at least 9.5 Watts per milliliter of blood flow per second.

14. A method as recited in claim 12, wherein the blood is removed from and returned to the victim using a concentric double lumen cannula.

15. A method as recited in claim 12, wherein the method includes the step of injecting gaseous oxygen into the exposure cell.

16. A method as recited in claim 12, wherein the method includes the step of maintaining the temperature of blood below the temperature that the blood degrades, while the blood is outside of the victim.

17. A method as recited in claim 12, wherein the method includes the step of capturing and isolating the disassociated carbon monoxide.

18. A method as recited in claim 12, wherein the method causes carbon monoxide poisoned blood to be removed from the victim at 500 ml per minute, and includes the step of capturing and isolating the disassociated carbon monoxide from the blood and the environment of the system.

* * * * *